United States Patent [19]

Bergins et al.

[11] Patent Number: 5,969,196

[45] Date of Patent: Oct. 19, 1999

[54] PROCESS FOR PREPARING 3,5-DIMETHYLPHENOL

[75] Inventors: Wolfgang Bergins, Castrop-Rauxel; Jörg Talbiersky, Dorsten, both of Germany

[73] Assignee: Rutgers VFT AG, Castrop-Rauxel, Germany

[21] Appl. No.: 09/067,301

[22] Filed: Apr. 27, 1998

[30] Foreign Application Priority Data

May 3, 1997 [DE] Germany .............................. 197 18 852

[51] Int. Cl.⁶ .................................................... C07C 37/50
[52] U.S. Cl. ........................... 568/805; 568/799; 568/377
[58] Field of Search .................................... 568/377, 716, 568/799, 805, 806

[56] References Cited

U.S. PATENT DOCUMENTS 3,641,166  2/1972  Ruhl et al. ........................... 260/621 R

FOREIGN PATENT DOCUMENTS 2166365  5/1986  United Kingdom .

*Primary Examiner*—Shailendra Kumar
*Assistant Examiner*—Sreeni Padmanabhan
*Attorney, Agent, or Firm*—Hedman, Gibson & Costigan, P.C.

[57] ABSTRACT

For the preparation of 3,5-dimethylphenol by catalytic demethylation of isophorone in the gas phase in the presence of a metal or a metal alloy as catalyst, an isophorone-containing process stream is guided through reaction zones that contain said catalyst, whereby the reactivity of the catalyst varies in the reaction zones and the process stream between these reaction zones is thermostated in zones that do nor contain any catalyst, whereby the residual isophorone is greatly reduced, and the yield of 3,5-dimethylphenol is increased.

2 Claims, No Drawings

PROCESS FOR PREPARING 3,5-DIMETHYLPHENOL

BACKGROUND, SUMMARY AND DESCRIPTION OF THE INVENTION

This invention relates to a process for preparing 3,5-dimethylphenol by catalytic demethylation of isophorone in the gas phase in the presence of a metal catalyst.

A corresponding process is disclosed in DE 1 768 875 B1 in which 4 to 17% residual isophorone is found in the crude product after a contact time of approximately 135 seconds. The maximum running time for the laboratory reactor was 135 hours. When the process of this patent was transferred to a large scale using a circulating-gasheated tubular reactor, it was shown that long reactor running times of 1,500 to 2,000 hours can only be attained with a relatively short contact time of 41 seconds. To avoid further shortening the reactor running time due to the formation of carbon on the catalyst, fresh catalyst must be used. When using a feed rate of 450 l/h, a reaction temperature of 550° C. and a pressure of 10 bar the residual isophorone in the crude product is approximately 9%.

Such high isophorone concentration in the crude product proves to be a great disadvantage when, in a further step, the crude 3,5-dimethylphenol is purified by means of crystallization. The isophorone passes on into the mother liquor which is rectified to obtain the 3,5-dimrethylphenol contained therein. Since isophorone and 3,5-dimethylphenol form an azeotrope, the presence of isophorone reduces the yield of distillation. In order to avoid a reduction in yield, the 3,5-dimethylphenol/isophorone fraction has to undergo special treatment. After leaching and distillation, 3,5-dimethylphenol is obtained with a purity of 96% purity. The yield of 3,5-dimethylphenol from this process fluctuates between 55 and 60% with reference to the amount of isophorone used.

In addition, reintroduction of regenerated catalyst that has been used several times into the reactor causes problems since, for example, the reactivity of the catalyst is greatly increased by the increase in surface area, which makes the process difficult to control.

The problem underlying the present invention is to provide a process that allows long reactor running times, a low residual isophorone content (less than 3%), higher yield of 3,5-dimethylphenol, associated therewith and a reduction of the amount of catalyst used.

This problem is solved by a process for preparing 3,5-dimethylphenol by means of catalytic demethylation of isophorone in the gas phase in the presence of a metal or a metal alloy as catalyst, wherein an isophorone-containing process streae is guided through reaction zones containing said catalyst, whereby the reactivity of said catalyst varies in said reaction zones, and the temperature of the process stream is thermostated between said reaction zores.

According to the invention, varying the reactivity of the catalyst in the reaction zones means the following: The reaction zones in the reactor contain catalyst with different degrees of activity. Different degrees of catalyst reactivity may be obtained by using fresh or used catalyst or mixtures of both. In one preferred embodiment, the process stream is subsequently guided over a fresh catalyst, a regenerated catalyst, and once again a fresh catalyst. In addition, two reaction zones that contain regenerated catalyst and are separated by cooling zones may be placed between the reaction zones containing fresh catalyst.

The process stream is thermostated in between the catalyst containing reaction zones to release reaction heat in the cooling zones. Thermostating may be achieved by the absence of a chemical reaction in the cooling zones, whereby no additional heating of the process stream containing the end product takes place.

The reaction is exothermic. As reactor preferably a tubular reactor is used that can be heated with circulating gas. The tubular reactor is filled with catalyst in such a manner that zones filled with catalyst alternate with zones free of catalyst. Suitable catalysts are metal catalysts and metal allow catalysts, e.g. steel alloys. Preferred catalysts are chromium-nickel-steel alloys, for example, the alloy X12 CrNi 18 9 (DIN 17006). The reaction temperature of the process according to the invention is preferably 450–600° C.

With the process according to the invention, the crude product contains only 1.5% residual isophorone. This corresponds to an improvement in yield of 5% over the prior art process. The running time is 2,000 hours. In addition, a catalyst may be used that has been regenerated several times having a reactivity that is greater than that of fresh catalyst by a factor of <10 without the disadvantage of reducing the running time by approximately 60%. This clearly saves costs in regard to catalyst consumption.

The process according to the invention will be explained in further detail in the following example.

EXAMPLE

A tubular reactor made from a chromium/nickel steel alloy with column packing of the same material was used. The reactor was filled in such a manner, that fresh catalyst was placed in the first reaction zone, which was followed by a catalyst-free zone in the tubular reactor. This was followed by a reaction zone having regenerated catalyst, a catalyst-free zone, and then a reaction zone having regenerated catalyst. A reaction zone having fresh catalyst directly followed this reaction zone.

The activity of the regenerated catalyst in the respective zones of the reactor was approximately 4 times that of the fresh catalyst in the reactor, which corresponds to a running time of approximately 1,800 h. The volume of the reactor was 450 l.

The throughput was 458 kg isophorone per hour at 552° C. and 9.5 bar. The dwell time was 72 sec., and the test period was 1,600 h. The effective volume of the zones with fresh contact was 75 ml in each case, that of the regenerated catalyst was 56 ml, and that of the catalyst-free zones was 94 m.

The residual isophorone in the crude product was 1.5%. The yield was 63% 3,5-dimethyiphenol with reference to the weight of the isophorone used.

What we claim is:

1. A process for preparing 3,5-dimethylphenol by catalytic demethylation of a process stream comprising isophorone in the gas phase in the presence of a catalyst comprising a metal or a metal alloy, said process comprising reacting said process stream in at least one reaction zone comprising fresh catalyst and at least one reaction zone comprising regenerated catalyst, and wherein the temperature of the process stream between said reaction zones is thermostated.

2. A process according to claim 1 wherein said process comprises three reaction zones wherein the entrance and exit zones of the reactor apply fresh catalyst, and the middle zone of the reactor applies regenerated reactive catalyst.

* * * * *